(12) United States Patent
Ueno et al.

(10) Patent No.: US 6,639,092 B2
(45) Date of Patent: Oct. 28, 2003

(54) METAL SALT OF BINAPHTHOL DERIVATIVE AND METHOD FOR PREPARING THE SAME

(75) Inventors: Ryuzo Ueno, Nishinomiya (JP); Masaya Kitayama, Takarazuka (JP); Kenji Minami, Sennan (JP); Hiroyuki Wakamori, Hikami-gun (JP)

(73) Assignee: Kabushiki Kaisha Ueno Seiyaku Oyo Kenkyujo, Osaka-fu (JP)

( * ) Notice: Subject to any disclaimer, the term of this patent is extended or adjusted under 35 U.S.C. 154(b) by 17 days.

(21) Appl. No.: 10/106,114

(22) Filed: Mar. 27, 2002

(65) Prior Publication Data

US 2002/0156309 A1 Oct. 24, 2002

(30) Foreign Application Priority Data

Mar. 27, 2001 (JP) ........................................ 2001-090108

(51) Int. Cl.$^7$ .................................................. C07F 3/06
(52) U.S. Cl. ........................................ 556/132; 556/184
(58) Field of Search .................................. 556/132, 184

(56) References Cited

U.S. PATENT DOCUMENTS

| | | | | |
|---|---|---|---|---|
| 3,223,720 A | * | 12/1965 | Casadio | |
| 3,491,135 A | * | 1/1970 | Krueger | |
| 4,772,724 A | * | 9/1988 | Wright | |
| 5,990,332 A | * | 11/1999 | Sukata | |
| 6,060,615 A | * | 5/2000 | Tsuruhara | |

* cited by examiner

Primary Examiner—Michael L. Shippen
(74) Attorney, Agent, or Firm—Sughrue Mion, PLLC

(57) ABSTRACT

Novel metal salts of binaphthol derivative are provided. The metal salts of the present invention are those represented by the formula of either (1) or (2):

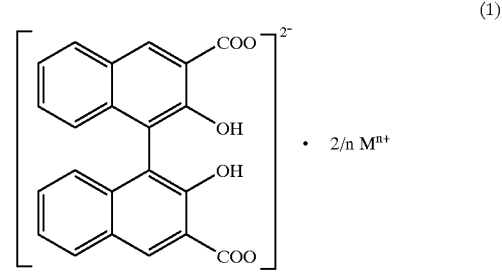

(1)

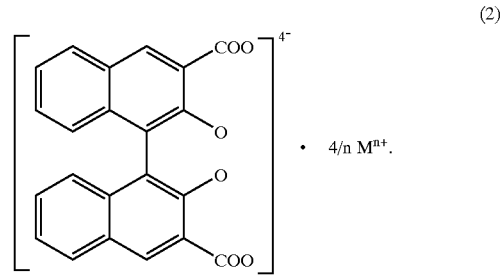

(2)

The present invention also provides a method for preparing the same from the corresponding binaphthalene derivative.

8 Claims, 3 Drawing Sheets

METAL SALT OF BINAPHTHOL DERIVATIVE AND METHOD FOR PREPARING THE SAME

BACKGROUND OF THE INVENTION

The present invention relates to a novel metal salt of binaphthol derivative and a method for preparing the same.

2,2'-dihydroxy-1,1'-binaphthalene-3,3'-dicarboxylic acid, a dimer of 2-hydroxynaphthalene-3-carboxylic acid has been proposed as toning agent in preparation of azo pigments (U.S. Pat. No. 4,804,415, the content of which is incorporated herein by reference). However, little has been known about metal salts of 2,2'-dihydroxy-1,1'-binaphthalene-3,3'-dicarboxylic acid. Only sodium salt has been proposed as an intermediate for ionic-coupling reaction with polytetrahydrofuran.

The instant invention provides a novel metal salt of a binaphthol derivative, which is expected to have variety of uses including charge control agent for an electrophotographic toner and image fixing modifier for inkjet recording paper used in inkjet printing systems.

In another aspect of the present invention, a method for preparing the metal salt of binaphthol derivative is also provided.

SUMMARY OF THE INVENTION

Based on extensive study on preparation of 2-hydroxynaphthalene-3-carboxylic acid dimers, the inventors have found a novel metal salt was able to be obtained by reacting the dimer with a determined amount of alkali metal compound, and then subjecting the same to metal exchange reaction with a bi- or trivalent metal compound.

Accordingly, the present invention provides a novel metal salt of binaphthol derivative comprising one of following formulae

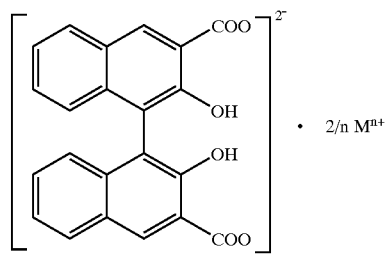

(1)

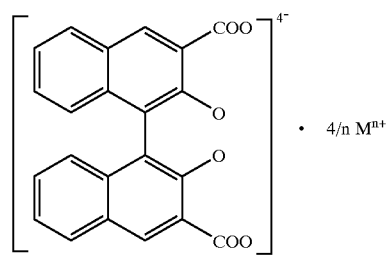

(2)

wherein n represents an integer of 2 or 3, M represents a bi- or trivalent metal atom.

In the metal salt of binaphthol derivative represented by general formula (I), both of the two carboxylic moieties on the respective naphthalene rings form salts with the metal.

In the metal salt of binaphthol derivative represented by general formula (2), all of the carboxylic and hydroxyl moieties on the respective naphthalene rings form salts with the metal.

In the above formulae, M represents bi- or trivalent metal such as aluminum, zinc, magnesium, calcium, strontium, barium, copper (II), iron(II), iron (III), cobalt (II), Nickel(II) and yettrium. Among them, aluminum and zinc are especially preferable.

The present invention also provides a method for preparing the metal salt of binaphthol derivative represented by formula (1) or (2).

The method for preparing the metal salt of binaphthol derivative represented by formula (1) comprises the steps of reacting a binaphthol derivative of formula (3):

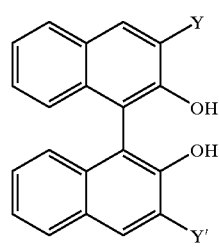

(3)

wherein Y and Y' represent carboxylic groups which may be esterified with an alkali metal compound 1.0–2.5 times molar amount of the binaphthol derivative to give alkali metal salt of the binaphthol derivative; and subjecting the resulting alkali metal salt to metal exchange reaction with a bi- or trivalent metal salt.

The method for preparing the metal salt of binaphthol derivative represented by formula (2) comprises the steps of reacting a binaphthol derivative of formula (3) with an alkali metal compound equal to or more than 3.0 times molar amount of the binaphthol derivative to give alkali metal salt of the binaphthol derivative; and subjecting the resulting alkali metal salt to metal exchange reaction with a bi- or trivalent metal salt.

According to the present invention, either of the metal salts of formula (1) or (2) can be selectivity obtained by controlling the molar amount of the alkali metal compound in relation to the starting material of binaphthol compound represented by formula (3).

In order to prepare the metal salt of formula (1), the molar amount of the alkali metal compound may be 1.0–2.5 times, preferably 2.0–2.2 times and more preferably about 2.0 times molar amount of the binaphthol derivative. The binaphthol derivative and the alkali metal compound are reacted to give an alkali metal salt of formula (4):

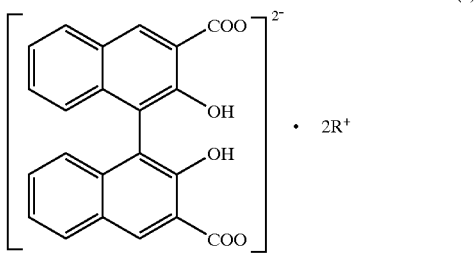

(4)

wherein R represents an alkali metal atom.

Then the obtained alkali metal salt is reacted with a bi- or trivalent metal salt by adding an aqueous solution of the bi- or trivalent metal salt dropwise to the reaction to effect metal exchange reaction. Accordingly, the metal salt of binaphthol derivative represented by formula (1) can be obtained.

The molar amount of the bivalent metal salt used in the metal exchange reaction may be 0.5–1.4 times molar amount of the alkali metal salt of formula (4). When the metal salt is of trivalent, the amount may be 0.4–1.0 times molar amount of the salt of formula (4).

When metal salt of binaphthol derivative of formula (2) is desired, the amount of the alkali metal compound is more than 3.0 times, preferably 4.0–5.0 times and more preferably 4.0–4.2 times molar amount of the starting binaphthol derivative. The binaphthol derivative and alkali metal are reacted to give an alkali metal salt of formula (5):

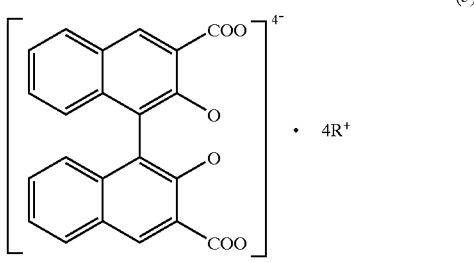

(5)

wherein R represents an alkali metal atom.

Then the obtained alkali metal salt solution is added dropwise to an aqueous solution of bi- or trivalent metal salt to effect metal exchange reaction. Accordingly, the metal salt of binaphthol derivative represented by formula (2) can be obtained.

The amount of bivalent metal salt used in the metal exchange reaction may be 2.0–2.5 times molar amount of the alkali metal salt of formula (5). When the metal salt is trivalent, the amount may be 1.5–1.9 times molar amount of the salt of formula (5).

Concentration of the aqueous solution of bi- or trivalent metal salt used in the present invention may preferably be 5–20 wt % and more preferably 5–10 wt %.

According to the present invention, either of the metal salts of formula (1) or formula (2) can be obtained selectively by controlling the molar amount of alkali metal compound in relation to the starting material of binaphthol compound.

DETAILED DESCRIPTION OF THE INVENTION

Figure 1:
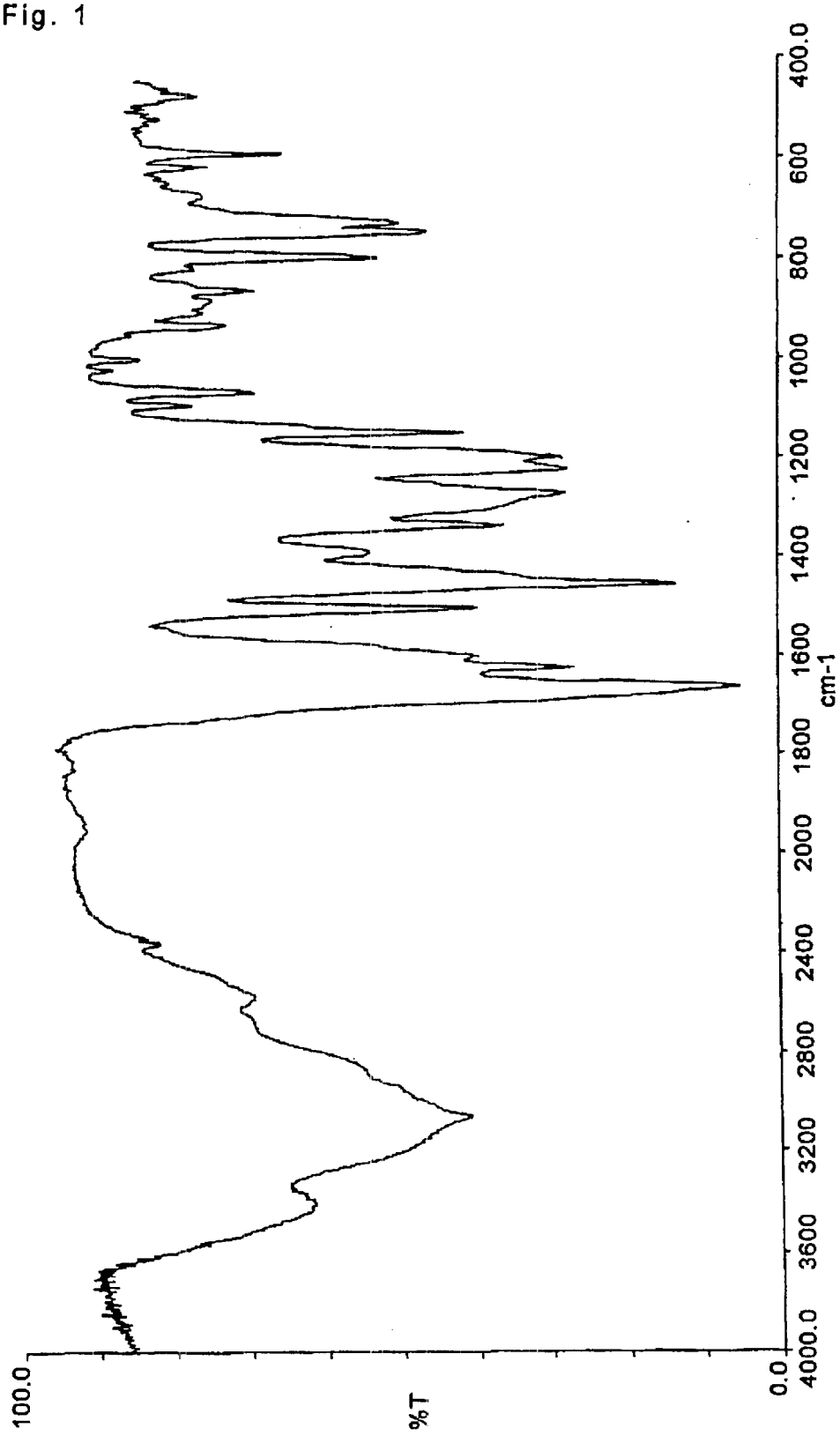
FIG. 1 is an infrared absorption spectrum (KBr) of 2,2'-dihydroxy-1,1'-binaphthalene-3,3'-dicarboxylic acid, which was used as starting material in the examples.

According to the present invention, the carboxylic groups which may be esterified of Y and Y' in the starting binaphthol derivative represented by formula (3) are preferably alkoxycarbonyl group having 1–6 carbon atoms such as methoxycarbonyl, ethoxycarbonyl, propyloxycarbonyl, isopropyloxycarbonyl, butoxycarbonyl, tert-butoxycarbonyl, pentyloxycarbonyl and hexyloxycabonyl, phenoxycarbonyl and phenacyloxycarbonyl groups. The aromatic groups contained in the above listed groups may have a substituent.

Examples of the substituents may include for example halogen atoms, halogenated lower alkyl, lower alkyl, lower alkoxy such as methoxy, phenyl, naphthyl, phenoxy, furyl, amino, toluidylamino, triadylamino, pyrimidylamino, benzoylamino, esterified carboxyl such as alkoxycarbonyl and phenoxy carbonyl groups, amidated carboxyl such as phenylcarbamoyl group, alkylaminosulfonyl and alkenyl group having 2–6 carbon atoms which may include aryl group.

In this specification and claims, the term "lower" represents a group having 1–6 carbon atoms.

According to the present invention, examples of alkali metal compound may include sodium hydroxide and potassium hydroxide, and sodium hydroxide is preferable because of its cost and availability.

Examples of the bi- or trivalent metal salt used in the present invention may include halide including chloride, bromide and iodide, sulfate, nitrate and acetate of aluminum, zinc, magnesium, calcium, strontium, barium, copper(II), iron(II), iron(III), cobalt(II) and yttrium. Among the above, water-soluble salts are preferable and aluminum chloride and zinc chloride are especially preferable.

Binaphtol derivative of formula (3) used as starting material may be prepared any known method. For example, U.S. Pat. No. 3,278,610 (disclosure of which is herein incorporated by reference) discloses a method comprising reacting a naphthol derivative in the presence of copper chloride, amine and oxygen in a media such as benzene. In addition, a method for preparing the desired derivative including the step of oxdating a naphthol derivative by iron chloride in an aqueous alkaline solution is well known among the art.

The metal salt of formula (1) or (2), especially aluminum or zinc salt, exhibits an excellent electrostatic property and therefore, is useful as charge controlling agent in electrophotographic toners and the like.

Further, the metal salt of the present invention provides high absorption capacity for absorbing vehicle of inkjet inks if incorporated in inkjet recording paper. Therefore, it is expected being useful as image fixing modifier for inkjet recording paper.

EXAMPLES

Preparation of Starting Compound 2,2'-dihydroxy-1,1'-binaphthalene-3,3'-dicarboxylic Acid

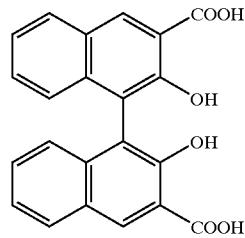

25.0 g of 2-hydroxynaphthalene-3-carboxylic acid was dispersed in 600 g of water, and 5.0 g of sodium hydroxide and 108 g of iron (III) chloride hexahydrate were added thereto. The mixture was allowed to react under reflux for 48 hours and then cooled to room temperature. The precipitates were collected by filtration and dissolved in 300 g of 5% aqueous sodium hydroxide. The solution was treated with activated carbon and then, insoluble materials were removed. The filtrate was adjusted around pH2 and the precipitates were collected by filtration. The precipitates were washed well with water and dried to give 26.2g of crude crystal containing 2,2'-dihydroxy-1,1'-binaphthalene-3,3'-dicarboxylic acid.

Then, the crude crystal was dispersed into 300 g of 80% aqueous acetic acid and the mixture was refluxed for about 30 minutes. The mixture was cooled to room temperature and the precipitates were collected by filtration, washed well with water and dried to give 13.4 g of purified 2,2'-dihydroxy-1,1'-binaphthalene-3,3'-dicarboxylic acid.

The infrared spectrum (by KBr method) of the obtained compound is shown in FIG. 1.

EXAMPLE 1

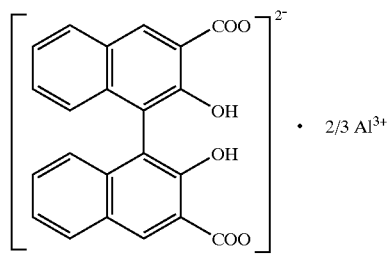

320 g (0.85 mol) of dimethyl 2,2-dihydroxy-1,1'-binaphthalene-3,3'-dicarboxylate was dispersed in 1000 g of methanol and 66 g (1.65 mol) of sodium hydroxide in 1000 g of water was added thereto. The mixture was reacted under reflux at about 70–80° C. for 12 hours. After the reaction, 70 g of aluminum chloride in 1000 g of water was added dropwise to the reaction at 60° C. After that, the mixture was heated again and stood for 2 hours under reflux. The reaction was cooled gradually to room temperature and the precipitates were collected by filtration. The precipitates were washed well with water and methanol, and dried to give 312 g of pale yellow powder of the desired compound. Al content: found. 4.61 wt %, calc. 4.35 wt %.

Figure 2:
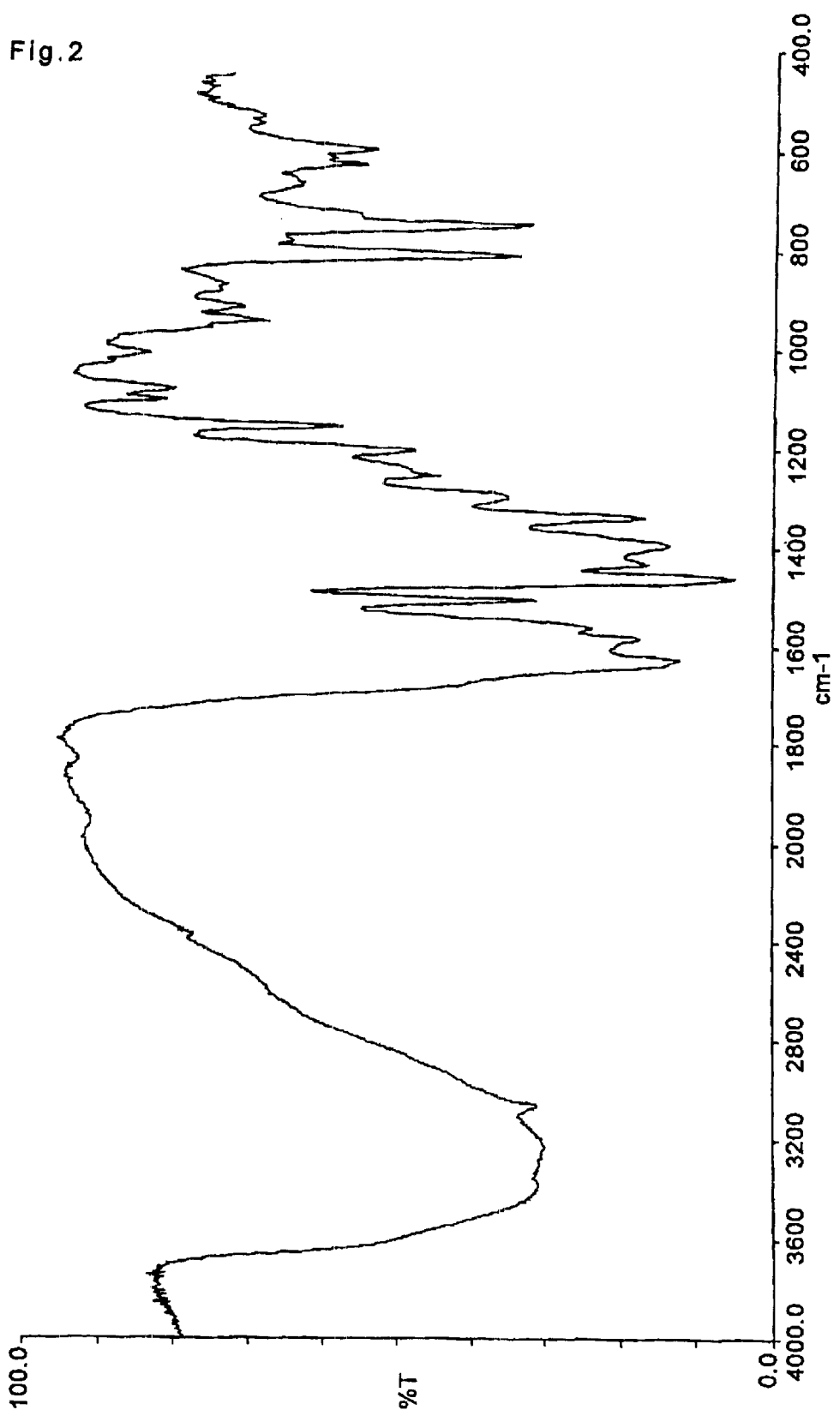
FIG. 2 is an infrared absorption spectrum (KBr) of the aluminum salt of binaphthol derivative obtained in Example 1.

The infrared spectrum (by KBr method) of the obtained compound is shown in FIG. 2.

EXAMPLE 2

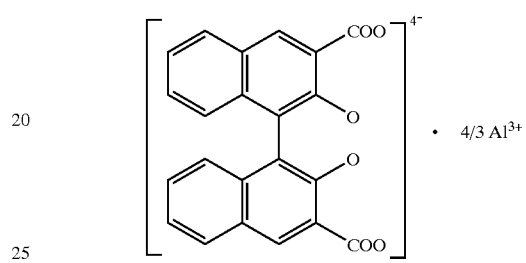

320 g (0.85 mol) of dimethyl 2,2'-dihydroxy 1,1'-binaphthalene-3,3'-dicarboxylate was dispersed in 1000 g of methanol, 134 g (3.4 mol) of sodium hydroxide in 1000 g of water was added thereto. The mixture was allowed to react under reflux at about 70–80° C. for 3 hours. After that, the reaction was added dropwise to 148 g of aluminum chloride dissolved in 1500 g of water at about 60° C. Then, the mixture was heated again and stood for 2 hours under reflux. Then the reaction was cooled gradually to room temperature and the precipitates were collected by filtration. The precipitates were washed well with water and methanol, and dried to give 319 g of pale yellow powder of the desired compound. Al content: found. 8.85 wt %, calc. 8.30 wt %.

Figure 3:
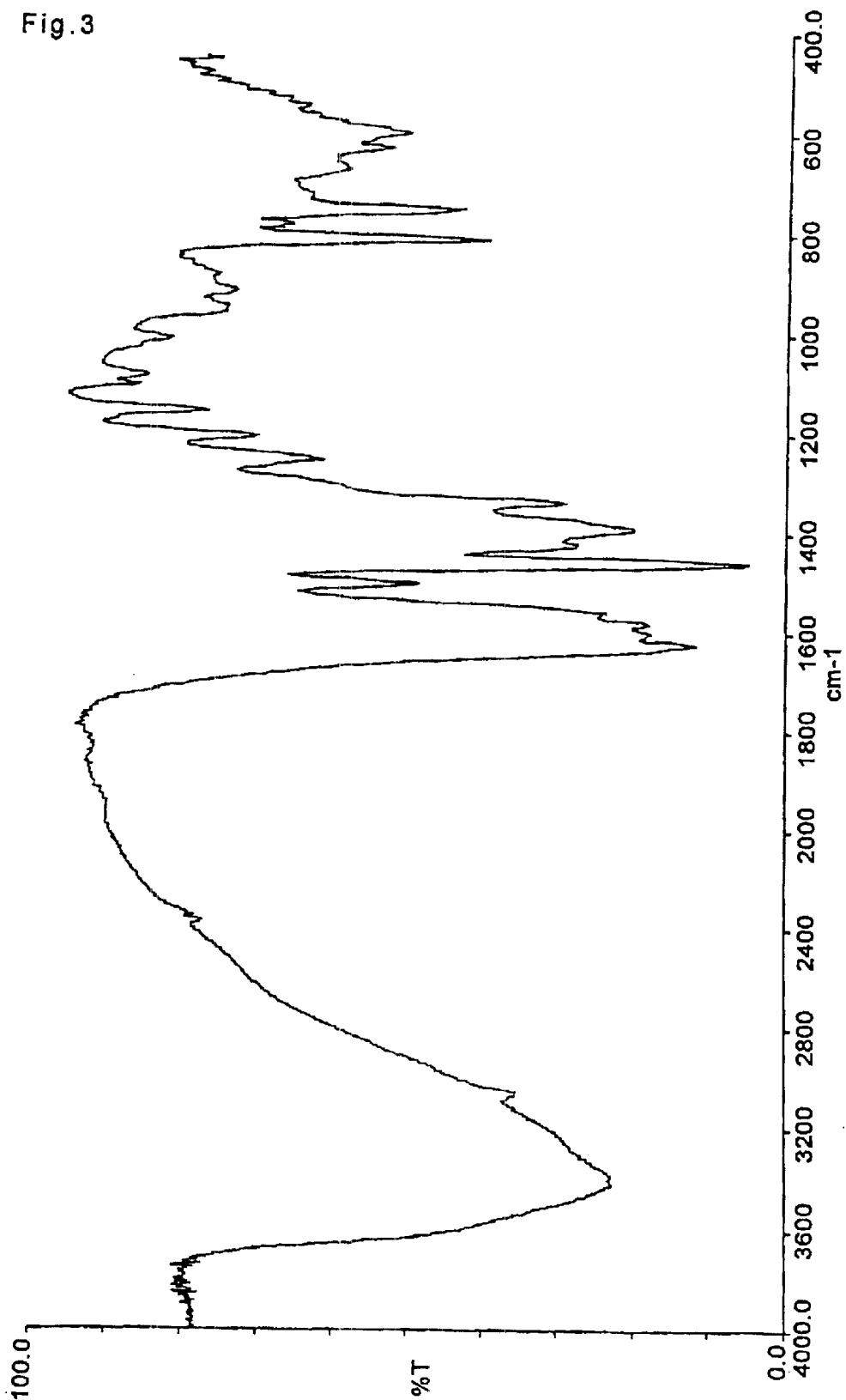
FIG. 3 is an infrared absorption spectrum (KBr) of the aluminum salt of binaphthol derivative obtained in Example 2.

The infrared spectrum (by KBr method) of the obtained compound is shown in FIG. 3.

IR spectra of the starting compound and the metal salts of examples 1 and 2 were compared. In the chart for metal salt of binaphthol derivative (FIGS. 2 and 3), peaks of around 1650 $cm^{-1}$ for the starting material of 2.2'-dihydroxy-1,1'-binaphthalene-3,3'-dicarboxylic acid were shifted to the lower wavenumber sides.

EXAMPLE 3

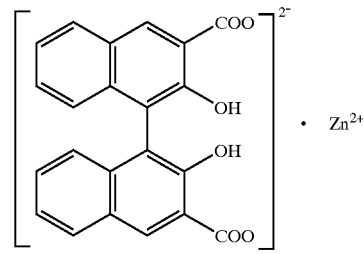

18.7 g (0.050 mol) of 2,2'-dihydroxy-1,1'-binaphthalene-3,3'-dicarboxylic acid was dispersed in 60 g of methanol, and 4.0 g (0.100 mol) of sodium hydroxide in 60 g of water was added thereto. The mixture was kept at about 60° C. for 2 hours. 6.8 g of zinc chloride in 100 g of water was added dropwise to the mixture at about 60° C. After that, the mixture was heated again and kept at the temperature under reflux for 2 hours. Then, the reaction was cooled gradually to room temperature and the precipitates were collected by filtration. The precipitates were washed well with water and methanol, and dried to give 20.6 g of grayish brown powder of the desired compound. Zn content: found 15.92 wt %, calc. 14.94 wt %.

EXAMPLE 4

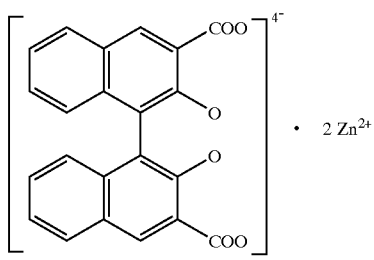

18.7 g (0.050 mol) of 2,2'-dihydroxy-1,1'-binaphthalene-3,3'-dicarboxylic acid was dispersed in 60 g of methanol and 8.0 g(0.200 mol) of sodium hydroxide in 60 g of water was added thereto. The mixture was kept at about 60° C. for 2 hours. Then, the mixture was added dropwise to 13.6 g of zinc chloride in 150 g of water at about 60° C. After that, the mixture was heated again and kept at the temperature under reflux for 2 hours. Then, the reaction was cooled gradually to room temperature and the precipitates were collected by filtration. The precipitates were washed well with water and methanol, and dried to give 21.1 g of grayish brown powder of the desired compound. Zn content: found 28.48 wt %, calc. 26.10 wt %.

EXAMPLE 5

The zinc salt obtained in Example 3 above and ferrite carrier ($\phi$=150 $\mu$m) at a weight ratio of 1:100 were mixed well. The frictional electrostatic charge was determined by means of blow-off powder electrostatic charge tester (#TB200, Toshiba Chemical Corp, Tokyo, Japan). The frictional electrostatic charge of thus obtained mixture was −64.9 $\mu$C/g.

The frictional electrostatic charge of the mixture consisting of the zinc salt obtained in Example 4 and the same ferrite carrier as above at a weight ratio of 1:100 was −44.0 $\mu$C/g.

EXAMPLE 6

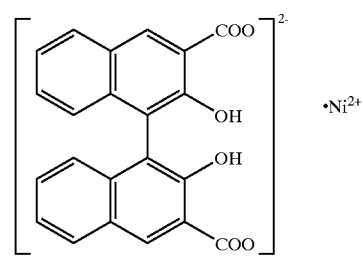

Nickel salt was prepared according to the same manner as Example 3 except for 12.4 g of nickel(II) acetate tetrahydrate was used instead of zinc chloride, 19.5 g of the desired compound was obtained as grayish brown powder. Ni content: found 12.57 wt %, calc. 13.62 wt %.

EXAMPLE 7

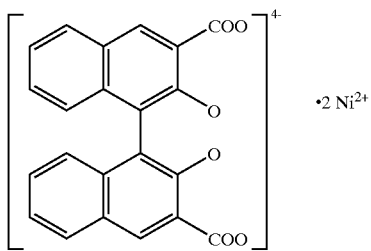

Nickel salt was prepared according to the same manner as Example 4 except for 24.8 g of nickel(II) acetate tetrahydrate was used instead of zinc chloride, 23.0 g of the desired compound was obtained as grayish green powder. Ni content: found 23.40 wt %, calc. 24.07 wt %.

What is claimed is
1. A metal salt of binaphthol derivative represented by either of formula (1) or (2) below:

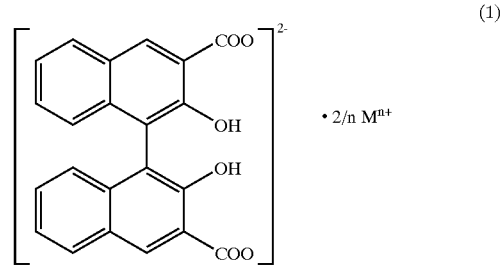

(1)

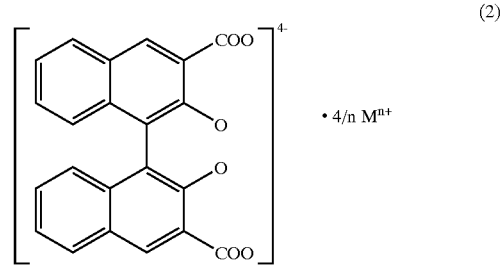

(2)

wherein n represents an integer of 2 or 3,
m represents a bi- or trivalent metal atom.

2. The metal salt of claim 1, wherein said metal atom is aluminum or zinc.

3. A method for preparing the metal salt of formula (I) comprising the steps of;

reacting a binaphthol derivative of formula (3):

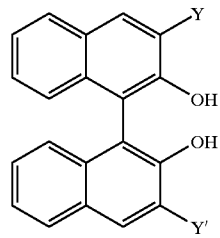

(3)

wherein Y and Y' represent carboxylic group which may be esterified with an alkali metal compound 1.0–2.5 times molar amount of the binaphthol derivative to give alkali metal salt of the binaphthol derivative, and subjecting the alkali metal salt to metal exchange reaction with a bi- or trivalent metal compound.

4. The method of claim 3, wherein the alkali metal compound is sodium hydroxide.

5. The method of claim 3, wherein the bi- or trivalent metal salt is aluminum chloride or zinc chloride.

6. A method for preparing the metal salt of formula (2) comprising the steps of;

reacting a binaphthol derivative of formula (3):

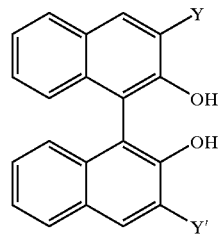

(3)

wherein Y and Y' represent carboxylic groups which may be esterified with an alkali metal compound equal to or more than 3.0 times molar amount of the binaphthol derivative to give alkali metal salt of the binaphthol derivative, and subjecting the alkali metal salt to metal exchange reaction with a bi- or trivalent metal compound.

7. The method of claim 6, wherein the alkali metal compound is sodium hydroxide.

8. The method of claim 6, wherein the bi- or trivalent metal salt is aluminum chloride or zinc chloride.

* * * * *